United States Patent [19]
Battista et al.

[11] Patent Number: 5,917,078
[45] Date of Patent: Jun. 29, 1999

[54] PROCESS FOR THE ISOLATION AND REMOVAL OF UNWANTED WATER FROM A CHEMICAL REACTION

[75] Inventors: Richard A. Battista, Dalton, Mass.; Francis S. Lo, Pasadena, Calif.; Robert L. Tatterson, Murcia, Spain

[73] Assignee: General Electric Company, Pittsfield, Mass.

[21] Appl. No.: 09/160,929

[22] Filed: Sep. 25, 1998

[51] Int. Cl.⁶ ...................................................... C07C 68/00
[52] U.S. Cl. ........................................... 558/274; 558/271
[58] Field of Search ............................................... 558/274

[56] References Cited

U.S. PATENT DOCUMENTS 5,399,734  3/1995  King, Jr. et al. .
5,498,742  3/1996  Buysch et al. .
5,625,091  4/1997  Buysch et al. .

FOREIGN PATENT DOCUMENTS 0085347    8/1983  European Pat. Off. .
04261142   9/1992  Japan .
4257546    9/1992  Japan .

*Primary Examiner*—Michael G. Ambrose

[57] ABSTRACT

An improved continuous process for removal of water from a process for producing organic carbonates, particularly diphenyl carbonate, by treating the water containing products of the reaction with a condensable stripping agent in a gaseous state and recycling a major portion of the water poor reaction products back to the reaction for producing the organic carbonate. The stripping agent, preferably n-pentane, is condensed upon removal from the water stripping step and recycled back to the water stripping step.

16 Claims, 1 Drawing Sheet

5,917,078

PROCESS FOR THE ISOLATION AND REMOVAL OF UNWANTED WATER FROM A CHEMICAL REACTION

FIELD OF THE INVENTION

This invention is related to an improved novel process for the removal of undesirable water from a chemical reaction for producing products which water is deleterious to the process and/or products produced therefrom. In particular, the products are carbonate esters, and more particularly diarylcarbonates, prepared by the carbonylation of alcohols, such as by the reaction of an organic hydroxyl compound with carbon monoxide and oxygen in the presence of a catalyst generally containing a noble metal of group VIII (b) of the Periodic Table of Elements and a co-catalyst. The process of this invention is a continuous process and employs a particular condensable water stripping agent. The process basically comprises a chemical reaction for producing products such as carbonate esters, employing a particular stripping agent to remove substantial amounts of water (dehydration) from the residue of a chemical reaction and then recycling the balance of the residue back to the reaction step. In preparing a diaryl carbonate, for example, the preferred diaryl carbonate is diphenyl carbonate.

BACKGROUND OF THE INVENTION

One known method of preparing an organic carbonates is by a direct procedure, which involves the oxidative reaction of an aromatic hydroxyl compound with carbon monoxide and oxygen in the presence of a noble metal catalyst and co-catalyst. The noble metal catalysts are the elements of group VIII (b) with palladium generally being the preferred noble metal used. The co-catalyst generally employed can be various manganese salts or cobalt salts in different oxidation states. In addition to these co-catalysts, a base, a quarternary ammonium salt and a desiccant can be used. A solvent may also be employed such as methylene chloride.

However, it has been determined that the removal of water from a reaction system in preparing a diaryl carbonate by carbonylations of alcohols leads to higher rates, higher selectively of the desired carbonate ester products and reduced degradation of catalytic species.

Techniques for the removal of water from organic carbonate synthesis from alcohols have been disclosed in the prior art. Several such processes include adsorption onto solid desiccants (U.S. Pat. No. 5,399,734 and EPO 0085347), distillation (JP04257546 and JP04261142) and stripping within the reactor with unreacted gaseous reactants or inert gaseous reactants (U.S. Pat. No. 5,498,742). However, these prior art processes have certain drawbacks. Adsorption onto solid desiccants such as molecular sieves is, by its very nature, a batch process in which the sieves must be periodically replaced or regenerated at high temperatures to provide for water removal capacity. This is economically undesirable in industrial practices.

The use of distillation, while potentially continuous, is undesirable due to the necessity of subjecting the reaction mixture to temperatures and pressures so that the water may vaporize.

Gaseous stripping within the reaction vessel, as previously disclosed, has disadvantages over this invention or several reasons: 1) stripping with inert components dilutes the reactant gases resulting in lower reactor productivity, 2) stripping with inerts is further limited to a 30% inert composition in the cited patent which is inferior to stripping with up to 100% inert gas in a separate vessel as per the disclosure in the present invention, 3) stripping within the reaction vessel limits the overall productivity of the system because optimal stripping and optimal reaction temperatures and pressures conditions do not coincide, 4) teachings in the cited patent do not describe use of a condensable stripping agent, thus requiring significant energy expenditure for recompression of non-condensable stripping gas to reaction pressure after water removal, and 5) absorbing or adsorbing or preferable condensing of water from the stripping gas in the cited patent is not as economic to the relatively low equipment and operating cost of the liquid-liquid separation of water as disclosed in this invention.

SUMMARY OF THE INVENTION

This invention relates to an improved process for the continuous removal of water in a continuous process for the preparation of chemical products wherein the presence of significant amounts of water, particularly where the water is by-product of the reaction, causes deleterious effects in the efficiency of the process and/or products of the reaction. The process of this invention is broadly directed to the preparation of any products from a chemical reaction where undesirable water is a by product of the reaction. Of particular interest are carbonate esters, particularly diaryl carbonates, and more particularly, diphenyl carbonates, prepared by the reaction of an organic hydroxyl compound, such as phenol, with carbon monoxide and oxygen in the presence of a catalytic system followed by the substantial removal of water from the reaction and then recycling the essentially water free materials back to the basic reaction. The presence of significant amounts of water in the system effects rates of reaction, selectivity of the desired end products such as carbonate ester products and degradation of the catalytic species employed in the reaction. The amount of water removed in the practice of this invention is at least about 75% by weight and preferably at least 90% by weight of the weight of the water present in the reaction medium prior to the stripping action and more particularly at least 95% by weight.

The continuous process of this invention comprises the steps of (1) producing a chemical product by a chemical reaction which has undesirable water at least as a by product, (2) separating two phases formed in the reaction consisting of a liquid phase and a vapor phase wherein the liquid phase comprises the product of the reactants, water, catalyst, and other ingredients and the vapor phase consists of volatile gases, (3) exhausting the vapor phase to the atmosphere, (4) feeding the liquid phase to a water stripping means wherein significant amounts of water are removed from the liquid phase by employing a particular condensable stripping agent in the stripping means, (5) separating the effluents from the stripping means which consists essentially of a dehydrated liquid phase and a stripping agent/water rich vapor phase, (6) recycling a portion of the dehydrated liquid phase to the reaction step (1) above, (7) condensing the stripping agent/water rich vapor phase which forms two phases, an essentially water phase and an essentially stripping agent phase, (8) separating the stripping agent phase, and (9) recycling the stripping agent back to the stripping step.

DETAILED DESCRIPTION OF THE INVENTION

Figure 1:
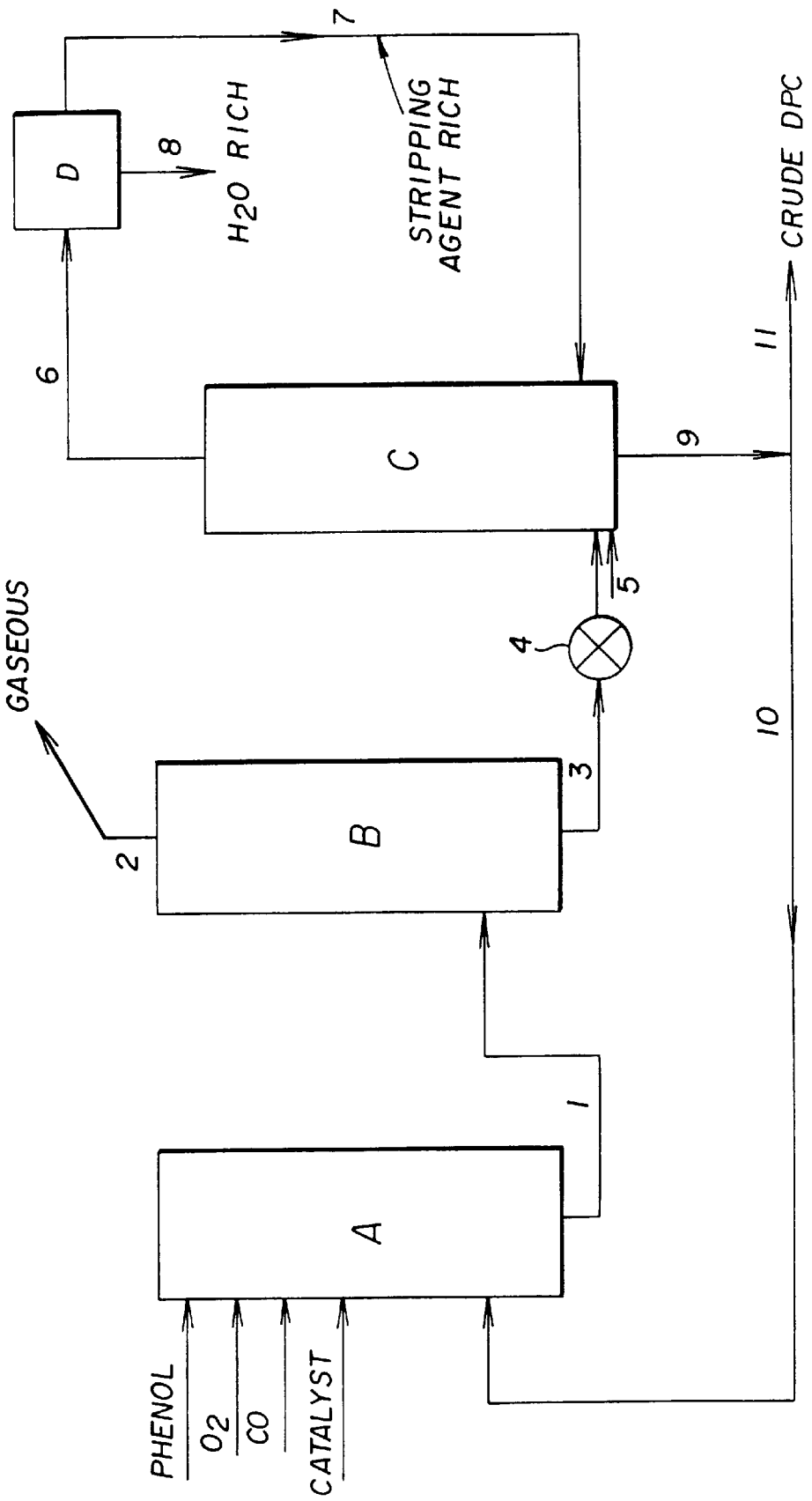
FIG. 1 shows a flow diagram of an apparatus, which continuously removes water.

The invention relates to a continuous improved process or preparing products by a chemical reaction wherein undesirable or deleterious water is at least a by product of the reaction. Preferably, the reaction is for preparing an organic carbonate of the following formula.

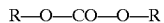

R—O—CO—O—R

Wherein R is independently an unsubstituted or substituted C-6–C-12 aryl radical, preferably an unsubstituted or substituted C-12 aryl radical and more particularly phenyl. The reaction is carried out by reacting an aromatic hydroxyl compound of the formula

R—OH wherein R has the meaning given above with carbon monoxide and oxygen in the presence of a catalyst such as a noble metal catalyst from a compound of a noble metal group VIII (b) of the Periodic Table. Optionally, a co-catalyst and/or a quarternary salt may also be employed in the reaction for producing the organic carbonate. The reaction residue comprises an organic carbonate, preferably diphenyl carbonate (hereinafter DPC) water and other ingredients. The improvement in the process of this invention is the removal of undesirable water by employing a particular stripping agent or combination of stripping agents. A portion of the reaction residue is then recycled back to the basic reaction process after removal of essentially most of the water.

This invention is directed to an improved continuous process for continuously removing water from a chemical reaction wherein the presence of water in a significant amount has deleterious effect on a chemical reaction process and/or the end products produced therefrom. Preferably the continuous process produces aromatic carbonate esters particularly diphenyl carbonate by reacting an organic hydroxyl compound with carbon monoxide and oxygen in the presence of a catalytic system followed by the removal of water wherein the improvement comprises the continuous removal of water by employing a particular condensable water stripping agent, recovering a mixture of an essentially dehydrated aromatic carbonate ester, phenol, catalyst and other ingredients, recycling a portion of the essentially dehydrated reaction mixture back to the basic reaction step, removing another portion of the reaction mixture in order to recover the carbonate ester, recovering and condensing the stripping agent and recycling the stripping agent back to the water stripping step.

The aromatic hydroxyl compounds that may be used in the process of preparing the carbonate esters of this invention are mono-, or poly-hydroxy compounds such as phenol, o-, m- or p-cresol, o-, m- or p-chlorophenol, o-, m- or p-ethylphenol, o-, m- or p-propylphenol, o-, m- or p-methoxyphenol, 2,6 dimethylphenol, 2,4-dimethylphenol, 3,4-dimethylphenol, 1-naphthol and 2-naphthol, xylenol, resorcinol, hydroquinone and bisphenol A. Aromatic organic mono hydroxy compounds are particularly preferred with phenol being the most preferred. In the case of substituents on the aromatic hydroxyl compound, the substituents are generally 1 or 2 substituents and are preferably from C-1 to C-4 alkyl, C-1 to C-4 alkoxy, fluorine, chlorine or bromine.

The catalyst employed herein may be the noble metal catalysts suitable for the reaction process and is composed of at least one metal of Group VIII, preferably palladium. The palladium material useful as a catalyst can be in elemental form or it can be employed as a palladium compound. Accordingly, palladium black or elemental palladium deposited on carbon can be used as well as palladium compounds, such as halides, nitrates, carboxylates, oxides and complexes involving such compounds such as carbon monoxide, amines, phosphines or olefins. The preferred palladium compounds are palladium (II) salts of organic acids including carboxylates with C-2 to C-6 aliphatic acids. Palladium (II) acetate is particularly preferred. There also can be used in combination with the palladium catalyst, tetraalkylammonium halide or tetraalkylphosphonium halide, such as the chlorides and bromides, particularly the bromides. Alkyl groups of the alkyl ammonium halides are primary and secondary alkyl groups containing about 1–8 carbon atoms. Tetra-n-butylammonium bromide is particularly preferred. There also can be used in combination with the palladium catalyst and the tetraalkylammonium halide at least one quinone and aromatic diol formed by the reduction of said quinone or a mixture thereof. 1,4-benzoquinone and hydroquinone are preferred. In addition, compounds such as 1,2-quinone and catechol, anthraquinone, 9,10-dihydroxyanthracene, and phenanthrenequinone also can be used.

In instances where the formation of an aromatic organic carbonates, such as diphenyl carbonate, is desired, manganese or cobalt cocatalysts also can be used. For example, cobalt or manganese compounds such as divalent or trivalent compounds, for example, salts such as halides and carboxylates and complexes with amines, diketones and carbon monoxide have been found effective. Cobalt (II) acetate is particularly preferred. It has been found that optimum selectivity i.e., optimizing the formation of aromatic carbonate and minimizing the formation of aromatic salicylate is achieved using the cobalt (II) catalyst.

An effective amount of the palladium catalyst is, for example, an amount sufficient to provide about 1 gram-atom of palladium, per 800–10,000 and preferably 5,000–10,000 moles of aromatic organic hydroxy compound. The other components of the palladium catalyst are, for example, per gram-atom of palladium, about 0.1–5.0, preferably about 0.5–1.5 gram-atoms of manganese or cobalt and about 5 to 150 and preferably about 20–50 moles of the tetraalkylammonium halide and about 10–60 and preferably about 25–40 moles of quinone and/or reduction product thereof.

Another catalyst that may be employed is lead oxide/hexamethylguanidinium bromide (PbO/HEG Br).

The quaternary salts that may be employed in the context of the present invention can be, for example, salts of ammonium or phosphonium substituted by organic radicals. ammonium salts and phosphonium salts which bear C-6 to C-10 aryl, C-7 to C-12 aralkyl and/or C-1 to C-20 alkyl radicals as organic radicals and a halide, tetrafluoroborate or hexafluorophosphate as anion are suitable for use in the process according to the invention. Ammonium salts which bear C-6 to C-10 aryl, C-1 to C-12 aralkyl and/or C-1 to C-20 alkyl radicals as organic radicals and a halide as anion are preferably used in the process according to the invention, particularly preferably tetrabutylammonium bromide.

The amount of such a quaternary salt is 0.1 to 50% by weight, based on the weight of the reaction mixture. This amount is preferably 0.5 to 15% by weight, particularly preferably 1 to 5% by weight.

In the process according to the invention, if desired, either organic or inorganic bases or mixtures thereof may be employed. Examples of inorganic bases which may be mentioned, without restricting the process according to the invention, are alkali metal hydroxides and alkali metal carbonates, alkali metal carboxylates or other salts of weak acids or alkali metal salts or aromatic hydroxyl compounds of the formula (II), e.alkali metal phenolates. Obviously, the hydrates of alkali metal phenolates can also be used in the process according to the invention. An example of such a hydrate which may be mentioned is sodium phenolate trihydrate. However, the amount of water added must preferably be measured in such a way that, per mol base, at most 5 mols of water are added. Higher water concentrations lead, inter alia, to poorer conversion rates and decomposition of carbonates formed. Organic bases which may be mentioned, without restricting the process according to the invention, are tertiary amines which bear as organic radicals C6–C10 aryl, C6–C12 aralkyl and/or C1–C20-alkyl or represent pyridine bases or hydrogenated pyridine bases, for example triethylamine, tripropylamine, tributylamine, trioctylamine, benzyldimethylamine, dioctylbenzylamine, dimethylphenethylamine, 1-dimethylamino-2-phenylpropane, pyridine, N-methylpiperidine, 1,2,2,6,6-pentamethylpiperidine. The base used is preferably an alkali metal salt of an aromatic hydroxyl compound, particularly preferably an alkali metal salt of the aromatic hydroxyl compound which is also to be converted to the organic carbonate. These alkali metal salts can be lithium salts, sodium salts, potassium salts, rubidium salts or caesium salts. Lithium phenolate, sodium phenolate and potassium phenolate are preferably used, particularly preferably sodium phenolate.

A base may be added to the reaction mixture as a pure compound in solid form or as a melt. In a further embodiment of the invention, the base is added to the reaction mixture as a solution which contains 0.1 to 80% by weight, preferably 0.5 to 65% by weight, particularly preferably 1 to 50% by weight of the base. The solvents which may optionally be used here are both alcohols or phenols, such as the phenol to be reacted, and inert solvents. Examples of solvents which may be mentioned are dimethylacetamide, N-methylpyrrolidinone, dioxane, t-butanol, cumyl alcohol, isoamyl alcohol, tetramethylurea, diethylene glycol, halogenated hydrocarbons (e.g. chlorobenzene or dichlorobenzene) and ethers. The solvents may be used alone or in any combination with each other.

A base, if used, is added in an amount independent of the stoichiometry. The ratio of palladium to base is preferably chosen in such a way that, per mol of palladium, 0.1 to 500, preferably 0.5 to 200, particularly preferably 0.9 to 130 equivalents of base are used.

While the above description is directed to the reaction process for producing the aromatic hydroxyl compound, such as and preferably diphenyl carbonate, this invention is directed to the unique continuous removal of undesirable water in a process for preparing products by a chemical reaction wherein the presence of water is undesirable having an effect on the process and/or products produced from the reaction. The advantages of removing water have been disclosed above.

The improved continuous process of this invention comprises the steps of preparing a chemical product by initiating a chemical reaction wherein the reaction residue of which contains water at least as a by-product; contacting the water containing reaction residue with a particular condensable water stripping agent having a boiling point less than the operating temperature for any given pressure employed in the stripping step and which is further immiscible with water; condensing the stripping agent; recycling the condensed stripping agent back to the stripping step; recycling a major portion of the essentially dehydrated or substantially water poor reaction residue mixture back to the basic chemical reaction step; and recovering a minor portion of the essentially dehydrated reaction residue in order to isolate the product of the chemical reaction.

Preferably, the improved continuous process of this invention is directed to preparing an essentially dehydrated or substantially water poor aromatic hydroxyl compound composition which improved process comprises the steps of (1) producing an organic hydroxyl compound by reacting an aromatic hydroxy compound with carbon monoxide and oxygen in the presence of a catalyst, (2) contacting the reaction residue of step (1) containing water and other ingredients with a condensable water stripping agent that is essentially gaseous at the temperature and pressure employed in the stripping step, (3) recovering from the stripping step a liquid phase which is essentially a dehydrated reaction residue and a gaseous phase which is essentially a stripping agent/water rich phase, (4) separating the two phases of (3) above, (5) condensing the stripping agent/water rich phase wherein two phases are formed, a stripping agent phase and a water phase, (6) recycling the stripping agent back to the stripping step, (7) recycling a major portion of the essentially dehydrated reaction residue back to reaction step (1), and (8) recovering a minor portion of the essentially dehydrated reaction residue for further recovery of the organic hydroxyl compound.

In the stripping step of the preferred improved process of this invention, a liquid phase and a vapor phase exit the water stripping step after contacting the reaction residue with the stripping agent. The liquid dehydrated reaction residue phase comprises a mixture of organic hydroxyl compound preferably diphenyl carbonate (DPC), catalyst, some water and other ingredients, a major portion of which is recycled to the basic reaction step and the balance is removed from the process for recovery of DPC. The gaseous vapor phase is comprised of vaporized stripping agent, water and minor amounts of other vaporous products. The vapor phase is condensed wherein two phases are formed, a stripping agent rich phase and a water rich phase. The stripping agent rich phase is returned to the stripping step. Each phase may also contain trace amounts of other components, particularly the water rich phase. It may be desirable to recover these trace amounts of ingredients such as phenol and other water soluble components from or entrained in the water rich phase. Subsequent processing of the water rich phase may be made by those processes known in the art to recover the material and render the water suitable for disposal. Such other materials in the stripping agent rich phase may be removed by known processes to those skilled in the art or allowed to accumulate and/or removed by a purge stream with concurrent stripping agent make-up.

The stripping agent phase recovered from the stripping step may also have additional stripping agent added thereto before recycling back to the stripping step with or without prevaporization of the stripping agent which can be achieved, if desired, through a heat exchanger or optionally dried to a lower total water content in order to achieve the highest stripping performance in the stripping step. Drying may be achieved by such means as passing the stripping agent over a physical drying agent such as molecular sieves or by contact with a chemical drying agent, such as anhydrides, or by distillation.

The above water removal process or dehydration process of this invention has the advantage over the prior art of (1) being coupled to the reaction system such as a carbonate ester reaction as a loop in that both withdrawing and discharging reaction mixture from and to the reaction system, which loop flow may be advantageously varied to achieve optimal extent of drying, (2) being an independent system from the reaction system, the process conditions of each may be individually optimized, and (3) being an essentially condensable stripping agent when in the condensed form, the system is then able to use pumps and not compressors which makes lower capital and operating costs.

The stripping agent/water rich vapor phase may then be separated into a stripping agent rich phase and a water rich phase by condensing at a reasonable condensing temperature of from about −25° F. to about 90° F. depending on the condensing medium employed such as brine, glycol or cooling water and the like. Cooling water may be preferable because of lower cost.

The stripping agent employed in the process of this invention is such that (1) it does not lead to undesirable reactions in the water removal system or in the reaction system when recycled back to the reaction process, (2) it is essentially immiscible with water in the liquid phase, and (3) it is essentially a vapor at the temperature and pressures maintained in the stripping process.

The process of this invention is a continuous process and as such achieves a material balance at steady state equilibrium. Output must equal input, i.e. that liquid phase removed from the system (stripping step) must equal that which is concurrently fed into the reaction step other than the recycled liquid phase from the stripping step. In one embodiment, the process comprises reacting an organic hydroxyl compound with carbon monoxide and oxygen in the presence of catalyst system, contacting the mixture of the reactants from the reaction with a particular stripping agent to remove water, recovering two phases comprising a vaporous phase and liquid phase, which liquid phase is comprised of DPC, some water and other ingredients, recycling a major portion of said liquid phase to the reaction step and the balance of said liquid phase is removed to recover DPC, condensing the stripping agent/water rich vaporous phase wherein a stripping agent rich phase and a water rich phase if formed and separating the stripping agent rich phase from the water rich phase. Other materials may also be present in the vaporous phase.

In a preferred embodiment, the process is a continuous water removal process comprising the steps of (1) forming a carbonate ester by charging a reactor with reactants comprised of an aromatic organic hydroxy compound, a catalyst in an amount sufficient to catalyze the carbonylation of the hydroxy compound, oxygen and carbon monoxide, (2) reacting the reactants at a temperature of about 40° C. to about 175° C. and of a pressure of about 1 to about 150 bar, (3) contacting the residue of the reaction which contains unwanted water with a condensable water stripping agent in a stripping column and at a temperature that is less than that which degrades the catalyst and which is above the freezing temperature of the residue of the reactants of step (2) above and wherein two phases are formed, a vapor phase and a liquid phase, (4) removing the two phases from the stripping column which vapor phase comprises a stripping agent/water phase and may contain other volatile components and which liquid phase is essentially dehydrated and comprises a carbonate ester, phenol and a minor amount of water, (5) recycling a major portion of the dehydrated liquid phase back to the carbonate ester reaction step, (6) removing the other portion of the dehydrated liquid phase to a recovery system for recovering carbonate ester therefrom, and (7) condensing the stripping agent/water rich phase wherein two phases are formed, a stripping agent phase and a water phase which stripping agent phase is then returned to the stripping column.

Preferably, the stripping agent has a boiling point of about 0° C. to less than about 100° C., preferably less than 70° C. and, more particularly, less than the operating temperature for any given pressure employed in the stripping means or step, and is selected from, but not limited to:

1,2-dichloro 1,2,2,2 tetrafluoro-n-butane
dichlorofluoromethane
neopentane
fluorotrichloromethane
isopentane
n-pentane
dichloroethylene
1,2-dibromotetrafluoroethane
cyclopentane
hexane-4
isohexane
hexane-3
hexane-5
n-hexane, or
mixtures thereof The preferred stripping agent is n-pentane.

Another embodiment of this invention for the removal of water consists of a unique combination of a stripping column, a liquid-liquid separation stage and a stripping solvent with special properties. A liquid stream comprised of reactants, inerts materials, homogeneous catalysts and reaction products including undesirable water from a reaction vessel are fed to a column in which the liquid stream is brought into contact with an essentially gaseous stripping agent. Water, and other materials of high volatility under the pressure and temperature in the stripping column, are removed overhead in a vapor state. The vaporous materials comprising stripping agent, water and other stripped components enter a condenser, operated in such a manner that, at a minimum, the vaporous materials comprised of water and stripping agent are condensed into two immiscible liquid phases a stripping agent phase and a water phase. The water containing phase is removed and the stripping agent phase is recycled to the stripping column. The condensed and isolated stripping agent, which may contain some water, may preferably be dried prior to its application as a stripping gas by passing over a physical drying agent such as molecular sieves or contact with a chemical drying agent such as anhydrides or distillation or other commonly known means. The preferred embodiment is the use of a distillation column for drying the stripping agent. It also may be prevaporized before returning the stripping agent to the stripping step.

In a preferred embodiment, the process comprises the continuous isolation or removal of a significant portion of water from the process can be described by referring to FIG. 1, a flow drawing of a preferred embodiment of this invention. While this invention is directed to the continuous removal of undesirable water from a chemical reaction process, the preferred chemical reaction is the preparation of a carbonate ester, preferably diphenyl carbonate. In FIG. 1, reactants phenol, oxygen, carbon monoxide and catalyst are fed to reactor vessel A wherein the reaction of the additives is carried out at a temperature of about 30° C. to about 200° C., preferably about 40° C. to about 120° C. and at a pressure of about 1 to about 150 bar, preferably about 5 to about 100 bar. Stream 1 consisting of a mixture of essentially diphenyl carbonate, phenol, water, catalyst, dissolved carbon monoxide, oxygen, carbon dioxide and other inert materials is fed to a vapor-liquid disengagement vessel B operated at a reduced pressure to separate gaseous phase from liquid phase which gaseous phase is removed from vessel B through stream 2. The liquid phase containing the liquid materials less volatile gaseous materials is pumped by pump 4 from vessel B through stream 3 which is fed to vessel C, a gas-liquid stripping vessel or column. Substantially, simultaneously therewith stream 5 is also fed to vessel C which vessel is maintained at pressures and temperatures for stripping water from feed stream 3. The selected stripping agent is as disclosed previously herein. In vessel C, gas-liquid contact is made between gaseous stripping agent and liquid components of stream 3. Stream 6 consists essentially of gaseous products comprising stripping agent and water existing vessel C through stream 6. Gaseous stream 6 is condensed and separated into a liquid water rich phase and a liquid stripping agent rich phase in condensation vessel D. Liquid stripping agent rich phase stream 7 is returned to vessel C while liquid water rich phase is removed from the system via stream 8. Liquid stream 9, essentially a dehydrated liquid stream, is comprised of crude diphenyl carbonate, phenol, catalyst, low amounts of water and other inert ingredients and may contain some residue of other volatile components the major portion of such volatiles is removed through stream 6, and may include some stripping agent. Stream 9 is separated into stream 10 and stream 11 with a majority of the contents of stream 9 being recycled back to reactor vessel A through stream 10. Stream 11 essentially comprises crude diphenol carbonate and is low or essentially free of water due to the stripping of water in vessel C from the residue of the reactants fed to vessel C through stream 3. As stated previously, the amount of water removed is at least 75% by weight of the water, preferably at least 90% by weight and, more particularly, at least 95% by weight of water is removed.

In addition, the preferred embodiment may optionally employ means for further drying the condensed stripping agent rich phase to a lower water content before recycling to vessel C. The drying may be achieved by employing drying means such as a molecular sieve or a chemical drying agent such as anhydrides or by distillation.

The water rich phase stream 8 may also contain some quantities of phenol and other water soluble components stripped or entrained from stripping vessel C. Subsequent processing of the water rich stream 8 may be employed as known in the art to recover any materials of value and to render the water suitable for disposal.

It was determined that by employing pentane as the stripping agent, the stripping vessel (vessel C) could be run at a lower pressure (about 20 psig) resulting in a higher percentage of water being removed with less stripping agent. About 90% by weight of water was removed namely from 2,000 ppm to about 200 ppm of water. This further results in a reduction in costs.

While variations of this invention will be suggested to those skilled in the art, in view of the above disclosures, it is understood that they fall within the scope of the claims appended hereto.

What is claimed is:

1. An improved continuous process for the preparation of products by a chemical reaction wherein undesirable water is present at least as a by-product which process comprises the continuous removal of the undesirable water from the residue of the chemical reaction, the improvement comprising the steps of (1) contacting water containing residue of reactants from a chemical reaction with an inert essentially gaseous condensable stripping agent, (2) recovering from the stripping agent contact step an essentially dehydrated liquid phase comprised of the residue of reactants and a gaseous stripping agent/water rich phase, (3) removing the stripping agent/water rich gaseous phase, (4) condensing the stripping agent/water rich gaseous phase which forms two immiscible phases, a stripping agent rich phase and a water rich phase, (5) separating the stripping agent rich phase and water rich phase, (6) recycling the stripping agent phase back to stripping step (1), and (7) recycling at least a majority of the essentially dehydrated liquid residue of reactants back to the chemical reaction.

2. The process of claim 1 wherein the chemical reaction is the preparation of an organic carbonate by the oxidative reaction of an organic hydroxyl compound with carbon monoxide and oxygen in the presence of a catalyst.

3. The process claim 1 wherein the stripping agent is dried before recycling to the stripping step.

4. The process of claim 2 wherein a minor portion of the dehydrated liquid residue of reactants is removed from the process and the organic carbonate is recovered by purification of the dehydrated liquid residue containing the organic carbonate.

5. The process of claim 2 wherein the organic carbonate is a carbonate ester.

6. The process of claim 4 wherein the carbonate ester is diaryl carbonate.

7. The process of claim 6 wherein the diaryl carbonate ester is diphenyl carbonate.

8. The improved process of claim 1 wherein the inert stripping agent (1) does not lead to undesirable reactions in the water removal phase or in the dehydrated liquid is recycled back to the reaction step, (2) is condensable at a temperature above the freezing temperature of the components with the stripping agent, (3) is essentially immiscible with water in the liquid phase, and (4) is essentially a vapor at the operating temperature and pressures in the stripping step.

9. The improved process of claim 1 wherein the improvement comprises the steps of (1) preparing an organic carbonate by reacting an aromatic hydroxy compound with carbon monoxide and oxygen in the presence of a catalyst, (2) feeding the reaction product of step (1) to a stripping column, (3) contacting the reaction residue of step 1 in the stripping column with an inert condensable water stripping agent that is essentially gaseous at the temperature and pressure employed in the stripping column wherein a dehydrated liquid phase and a gaseous stripping agent/water phase is formed, (4) separating the dehydrated liquid phase and the stripping agent/water rich phase, (5) condensing the gaseous stripping agent/water rich phase wherein two immiscible liquid phases are formed one of which comprises a stripping agent rich phase and the other comprises a water rich phase, (6) separating the stripping agent phase formed in step 5 and recycling the stripping agent phase back to the stripping step, (7) recycling a major portion of the dehydrated liquid phase of step 3 back to reaction step 1, and (9) separating a minor part of the dehydrated liquid phase of step 3 for further recovery of the organic carbonate.

10. The improved process of claim 9 wherein the stripping agent is n-pentane.

11. The process of claim 9 wherein the reaction for preparing the organic hydroxyl compound is at a temperature of about 30° C. to about 200° C. and a pressure of about 1 bar to about 150 bar, and the water stripping step is at a pressure of about 0.1 to about 20 bar and a temperature of less than about 100° C.

12. The process of claim 9 wherein at least about 75% by weight of water is removed in the water stripping step.

13. The process of claim 11 wherein at least 95% by weight of water is removed.

14. The process of claim 9 wherein the condensed stripping agent is further dried to a lower water content by distillation before recycling back to the stripping step.

15. The process of claim 9 wherein the minor amount of the essentially dehydrated liquid phase is distilled to recover the organic carbonate.

16. The process of claim 15 wherein the organic carbonate is diphenyl carbonate.

* * * * *